(12) United States Patent
Nguyen et al.

(10) Patent No.: US 11,596,423 B2
(45) Date of Patent: Mar. 7, 2023

(54) SYSTEM FOR TREATING OCCLUSIONS IN BODY LUMENS

(71) Applicant: Shockwave Medical, Inc., Santa Clara, CA (US)

(72) Inventors: Hoa D. Nguyen, San Jose, CA (US); Camilo Perez Saaibi, Fremont, CA (US)

(73) Assignee: Shockwave Medical, Inc., Santa Clara, CA (US)

( * ) Notice: Subject to any disclaimer, the term of this patent is extended or adjusted under 35 U.S.C. 154(b) by 336 days.

(21) Appl. No.: 16/436,186

(22) Filed: Jun. 10, 2019

(65) Prior Publication Data
US 2019/0388110 A1  Dec. 26, 2019

Related U.S. Application Data

(60) Provisional application No. 62/688,110, filed on Jun. 21, 2018.

(51) Int. Cl.
*A61B 17/22* (2006.01)
*A61M 25/10* (2013.01)
*A61B 17/00* (2006.01)

(52) U.S. Cl.
CPC ..... *A61B 17/22012* (2013.01); *A61M 25/104* (2013.01); *A61B 2017/00154* (2013.01);
(Continued)

(58) Field of Classification Search
CPC ........ A61B 17/22022; A61B 17/22004; A61B 17/22012; A61B 2017/22025;
(Continued)

(56) References Cited

U.S. PATENT DOCUMENTS 3,051,862 A * 8/1962 Johnm ................... F23Q 3/006
313/146
3,413,976 A 12/1968 Roze
(Continued)

FOREIGN PATENT DOCUMENTS

AU 2009313507 B2 11/2014
CN 1269708 A 10/2000
(Continued)

OTHER PUBLICATIONS

Advisory Action received for U.S. Appl. No. 13/615,107, dated Nov. 6, 2015, 3 pages.
(Continued)

*Primary Examiner* — Kathleen S Holwerda
(74) *Attorney, Agent, or Firm* — Morrison & Foerster LLP

(57) ABSTRACT

The invention provides a system for treating an occlusion within a body lumen. The system may comprise an insulated outer sheath; an elongated conductive tube, wherein the insulated outer sheath is circumferentially mounted around the elongated conductive tube; and an insulated wire having a helically coiled portion at a distal end of the insulated wire. The coiled portion includes an exposed distal tip, and a distal portion of the elongated conductive tube is circumferentially mounted around the distal coiled portion of the insulated wire. When a voltage is applied across the insulated wire and the elongated conductive tube, a current is configured to flow from the exposed distal tip of the insulated wire to the elongated conductive tube to generate a plurality of cavitation bubbles. In an alternate embodiment, an elongated central electrode is used in place of the conductive tube.

30 Claims, 8 Drawing Sheets

(52) U.S. Cl.
CPC ............. *A61B 2017/22001* (2013.01); *A61B 2017/22007* (2013.01); *A61B 2017/22011* (2013.01); *A61B 2017/22021* (2013.01); *A61B 2017/22025* (2013.01); *A61B 2017/22042* (2013.01); *A61B 2017/22051* (2013.01); *A61B 2017/22094* (2013.01)

(58) Field of Classification Search
CPC .......... A61B 2017/22098; A61B 2017/22007; A61B 2017/22011; A61B 2017/22021; A61B 2017/22042; A61B 2017/22051; A61B 2017/22094; A61B 2017/00154; G10K 15/06; G10K 15/043; A61H 23/008; A61N 2007/0004; A61N 2007/0008; A61N 2007/0013; A61N 2007/0017; A61N 2007/0039
USPC .................................................. 606/127, 128
See application file for complete search history.

(56) References Cited

U.S. PATENT DOCUMENTS

| | | | |
|---|---|---|---|
| 3,785,382 A | 1/1974 | Schmidt-Kloiber et al. | |
| 3,902,499 A | 9/1975 | Shene | |
| 4,027,674 A | 6/1977 | Tessier et al. | |
| 4,030,505 A | 6/1977 | Tessier | |
| 4,662,126 A | 5/1987 | Malcolm | |
| 4,671,254 A | 6/1987 | Fair | |
| 4,685,458 A | 8/1987 | Leckrone | |
| 4,809,682 A | 3/1989 | Forssmann et al. | |
| 4,813,934 A | 3/1989 | Engelson et al. | |
| 4,870,953 A † | 10/1989 | Don Micheal | |
| 4,878,495 A | 11/1989 | Grayzel | |
| 4,900,303 A | 2/1990 | Lemelson | |
| 4,994,032 A | 2/1991 | Sugiyama et al. | |
| 5,009,232 A | 4/1991 | Hassler et al. | |
| 5,046,503 A | 9/1991 | Schneiderman | |
| 5,057,103 A | 10/1991 | Davis | |
| 5,057,106 A | 10/1991 | Kasevich et al. | |
| 5,061,240 A | 10/1991 | Cherian | |
| 5,078,717 A | 1/1992 | Parins et al. | |
| 5,103,556 A * | 4/1992 | Filip ............... | A61B 17/22022 29/825 |
| 5,103,804 A | 4/1992 | Abele et al. | |
| 5,125,928 A | 6/1992 | Parins et al. | |
| 5,150,717 A † | 9/1992 | Rosen | |
| 5,152,767 A | 10/1992 | Sypal et al. | |
| 5,152,768 A | 10/1992 | Bhatta | |
| 5,154,722 A † | 10/1992 | Filip | |
| 5,176,675 A | 1/1993 | Watson et al. | |
| 5,195,508 A | 3/1993 | Muller et al. | |
| 5,245,988 A | 9/1993 | Einars et al. | |
| 5,246,447 A | 9/1993 | Rosen et al. | |
| 5,254,121 A | 10/1993 | Manevitz et al. | |
| 5,281,231 A | 1/1994 | Rosen et al. | |
| 5,295,958 A | 3/1994 | Shturman | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | de la Torre et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | de la Torre et al. | |
| 5,697,281 A | 12/1997 | Eggers et al. | |
| 5,735,811 A | 4/1998 | Brisken | |
| 5,846,218 A | 12/1998 | Brisken et al. | |
| 5,931,805 A | 8/1999 | Brisken | |
| 6,007,530 A | 12/1999 | Dornhofer et al. | |
| 6,033,371 A | 3/2000 | Torre et al. | |
| 6,080,119 A | 6/2000 | Schwarze et al. | |
| 6,083,232 A | 7/2000 | Cox | |
| 6,113,560 A | 9/2000 | Simnacher | |
| 6,186,963 B1 | 2/2001 | Schwarze et al. | |
| 6,210,404 B1 | 4/2001 | Shadduck | |
| 6,210,408 B1 | 4/2001 | Chandrasekaran et al. | |
| 6,217,531 B1 | 4/2001 | Reitmajer | |
| 6,267,747 B1 | 7/2001 | Samson et al. | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O'Connor | |
| 6,406,486 B1 | 6/2002 | De La Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 † | 11/2003 | Rabiner | |
| 6,689,089 B1 | 2/2004 | Tiedtke et al. | |
| 6,736,784 B1 | 5/2004 | Menne et al. | |
| 6,740,081 B2 | 5/2004 | Hilal | |
| 6,755,821 B1 | 6/2004 | Fry | |
| 6,855,123 B2 | 2/2005 | Nita | |
| 6,989,009 B2 | 1/2006 | Lafontaine | |
| 7,087,061 B2 * | 8/2006 | Chernenko ...... | A61B 17/22022 604/22 |
| 7,241,295 B2 | 7/2007 | Maguire | |
| 7,505,812 B1 | 3/2009 | Eggers et al. | |
| 7,569,032 B2 | 8/2009 | Naimark et al. | |
| 7,873,404 B1 | 1/2011 | Patton | |
| 7,951,111 B2 | 5/2011 | Drasler et al. | |
| 8,162,859 B2 | 4/2012 | Schultheiss et al. | |
| 8,556,813 B2 | 10/2013 | Cioanta et al. | |
| 8,574,247 B2 | 11/2013 | Adams et al. | |
| 8,709,075 B2 † | 4/2014 | Adams | |
| 8,728,091 B2 | 5/2014 | Hakala et al. | |
| 8,747,416 B2 | 6/2014 | Hakala et al. | |
| 8,856,371 B2 | 10/2014 | Kariti et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,198,825 B2 † | 12/2015 | Katragadda | |
| 9,333,000 B2 | 5/2016 | Hakala et al. | |
| 9,421,025 B2 | 8/2016 | Hawkins et al. | |
| 9,433,428 B2 | 9/2016 | Hakala et al. | |
| 9,642,673 B2 | 5/2017 | Adams et al. | |
| 9,730,715 B2 | 8/2017 | Adams | |
| 9,993,292 B2 † | 6/2018 | Adams | |
| 9,999,788 B2 | 6/2018 | Gattiker et al. | |
| 10,226,265 B2 | 3/2019 | Ku et al. | |
| 10,765,440 B2 | 9/2020 | Tozzi | |
| 2001/0044596 A1 | 11/2001 | Jaafar | |
| 2002/0045890 A1 | 4/2002 | Celliers et al. | |
| 2002/0077643 A1 | 6/2002 | Rabiner et al. | |
| 2002/0077653 A1 | 6/2002 | Hudson et al. | |
| 2002/0177889 A1 | 11/2002 | Brisken et al. | |
| 2003/0004434 A1 | 1/2003 | Greco et al. | |
| 2003/0088262 A1 | 5/2003 | Bonnette et al. | |
| 2003/0176873 A1 | 9/2003 | Chernenko et al. | |
| 2003/0229370 A1 | 12/2003 | Miller | |
| 2004/0006333 A1 | 1/2004 | Arnold et al. | |
| 2004/0010249 A1 | 1/2004 | Truckai et al. | |
| 2004/0044308 A1 | 3/2004 | Naimark et al. | |
| 2004/0097963 A1 * | 5/2004 | Seddon ............... | A61B 17/221 606/127 |
| 2004/0097996 A1 | 5/2004 | Rabiner et al. | |
| 2004/0162508 A1 | 8/2004 | Uebelacker | |
| 2004/0193046 A1 | 9/2004 | Nash et al. | |
| 2004/0254570 A1 | 12/2004 | Hadjicostis et al. | |

(56) References Cited

U.S. PATENT DOCUMENTS

| | | |
|---|---|---|
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0085054 A1† | 4/2006 | Zikorus |
| 2006/0184076 A1* | 8/2006 | Gill .................. A61B 17/2202 601/3 |
| 2006/0190022 A1 | 8/2006 | Beyar et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0177085 A1 | 7/2009 | Maxwell et al. |
| 2009/0247945 A1 | 10/2009 | Levit et al. |
| 2009/0254114 A1 | 10/2009 | Hirszowicz et al. |
| 2009/0312768 A1† | 12/2009 | Hawkins |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0305565 A1† | 12/2010 | Truckai |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1* | 8/2011 | Diamant ............ A61B 18/1492 606/42 |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0203255 A1 | 8/2012 | Hawkins et al. |
| 2012/0221013 A1 | 8/2012 | Hawkins et al. |
| 2013/0030431 A1 | 1/2013 | Adams |
| 2013/0030447 A1 | 1/2013 | Adams |
| 2013/0116714 A1 | 5/2013 | Adams et al. |
| 2013/0150874 A1 | 6/2013 | Kassab |
| 2013/0158453 A1 | 6/2013 | Brouillette et al. |
| 2014/0005576 A1* | 1/2014 | Adams ............ A61B 17/22022 601/4 |
| 2014/0039513 A1* | 2/2014 | Hakala ............ A61B 17/22022 606/128 |
| 2014/0046229 A1 | 2/2014 | Hawkins et al. |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0214061 A1 | 7/2014 | Adams et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2015/0073430 A1 | 3/2015 | Hakala et al. |
| 2015/0238208 A1 | 8/2015 | Adams et al. |
| 2015/0238209 A1 | 8/2015 | Hawkins et al. |
| 2015/0320432 A1* | 11/2015 | Adams .................. A61M 25/09 606/128 |
| 2016/0151081 A1 | 6/2016 | Adams et al. |
| 2016/0183957 A1 | 6/2016 | Hakala et al. |
| 2016/0184570 A1 | 6/2016 | Grace et al. |
| 2016/0324534 A1 | 11/2016 | Hawkins et al. |
| 2016/0331389 A1 | 11/2016 | Hakala et al. |
| 2017/0135709 A1 | 5/2017 | Nguyen et al. |
| 2017/0231649 A1 | 8/2017 | Rabiner et al. |
| 2017/0311965 A1 | 11/2017 | Adams |
| 2018/0098779 A1 | 4/2018 | Betelia et al. |
| 2018/0360482 A1 | 12/2018 | Nguyen |
| 2019/0150960 A1 | 5/2019 | Nguyen et al. |
| 2019/0254692 A1 | 8/2019 | Hakala et al. |
| 2021/0085348 A1 | 3/2021 | Nguyen et al. |

FOREIGN PATENT DOCUMENTS

| | | |
|---|---|---|
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 0623360 A1 | 11/1994 |
| EP | 0647435 A1 | 4/1995 |
| EP | 2253884 A1 | 11/2010 |
| EP | 2359764 A1 | 8/2011 |
| EP | 2362798 B1 | 4/2014 |
| JP | 60-191353 U | 12/1985 |
| JP | 62-99210 U | 6/1987 |
| JP | 62-275446 A | 11/1987 |
| JP | 3-63059 A | 3/1991 |
| JP | 6-125915 A | 5/1994 |
| JP | 7-47135 A | 2/1995 |
| JP | 8-89511 A | 4/1996 |
| JP | 10-99444 A | 4/1998 |
| JP | 10-314177 A | 12/1998 |
| JP | 10-513379 A | 12/1998 |
| JP | 2002-538932 A | 11/2002 |
| JP | 2004-81374 A | 3/2004 |
| JP | 2004-357792 A | 12/2004 |
| JP | 2005-501597 A | 1/2005 |
| JP | 2005-95410 A | 4/2005 |
| JP | 2005-515825 A | 6/2005 |
| JP | 2006-516465 A | 7/2006 |
| JP | 2007-532182 A | 11/2007 |
| JP | 2008-506447 A | 3/2008 |
| JP | 2011-513694 A | 4/2011 |
| JP | 2011-520248 A | 7/2011 |
| JP | 2011-524203 A | 9/2011 |
| JP | 2011-528963 A | 12/2011 |
| JP | 2012-505050 A | 3/2012 |
| JP | 2012-508042 A | 4/2012 |
| JP | 6029828 B2 | 11/2016 |
| JP | 6081510 B2 | 2/2017 |
| WO | 1992/03975 A1 | 3/1992 |
| WO | 1996/24297 A1 | 8/1996 |
| WO | 1999/00060 A1 | 1/1999 |
| WO | 1999/02096 A1 | 1/1999 |
| WO | 2000/56237 A2 | 9/2000 |
| WO | WO-2000051502 A1 | 9/2000 |
| WO | 2004/069072 A2 | 8/2004 |
| WO | WO-2005034793 A2 | 4/2005 |
| WO | 2005/099594 A1 | 10/2005 |
| WO | 2006/006169 A2 | 1/2006 |
| WO | 2006/127158 A2 | 11/2006 |
| WO | 2007/088546 A2 | 8/2007 |
| WO | 2007/149905 A2 | 12/2007 |
| WO | 2009/121017 A1 | 10/2009 |
| WO | 2009/126544 A1 | 10/2009 |
| WO | 2009/152352 A2 | 12/2009 |
| WO | 2010/014515 A2 | 2/2010 |
| WO | 2010/014515 A3 | 2/2010 |
| WO | 2010/054048 A3 | 5/2010 |
| WO | 2011/094111 A2 | 8/2011 |

(56) References Cited

FOREIGN PATENT DOCUMENTS

| WO | 2011/143468 A2 | 11/2011 |
|---|---|---|
| WO | 2012/025833 A2 | 3/2012 |
| WO | 2013/059735 A1 | 4/2013 |
| WO | 2015/017499 A1 | 2/2015 |
| WO | 2016/109739 A1 | 7/2016 |

OTHER PUBLICATIONS

Advisory Action received for U.S. Appl. No. 12/482,995, dated Jun. 2, 2014, 3 pages.
Advisory Action received for U.S. Appl. No. 12/482,995, dated Sep. 29, 2011, 2 pages.
Advisory Action received for U.S. Appl. No. 12/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Bom et al., "Intra-arterial Ultrasonic Imaging for Recanalization by Spark Erosion", Ultrasound in Medicine & Biology, vol. 14, No. 4, 1988, pp. 257-261.
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiol, vol. 95, 2003, pp. 67-75.
Decision of Appeals Notice received for Japanese Patent Application No. 2011-534914, dated Oct. 17, 2016., 2 pages (Official copy only) (See Communication under 37 CFR § 1.98(a) (3)).
Decision to Grant received for European Patent Application No. 13756766.5, dated May 27, 2016, 2 pages.
Decision to Grant received for European Patent Application No. 09825393.3, dated Mar. 13, 2014, 2 pages.
Decision to Grant received for Japanese Patent Application No. 2011-513694, dated Oct. 7, 2014, 3 pages (Official copy only) (See Communication under 37 CFR § 1.98(a) (3)).
Extended European Search Report (includes Supplementary European Search Report and Search Opinion) received for European Patent Application No. 09763640.1, dated Oct. 10, 2013, 5 pages.
Extended European Search Report and Search Opinion received for European Patent Application No. 09825393.3, dated Feb. 28, 2013, 6 pages.
Extended European Search Report received for European Patent Application No. 13827971.6, dated Apr. 12, 2016, 8 pages.
Final Office Action received for U.S. Appl. No. 12/482,995, dated Jul. 22, 2011, 14 pages.
Final Office Action received for U.S. Appl. No. 12/501,619, dated Feb. 21, 2012, 12 pages.
Final Office Action received for U.S. Appl. No. 12/611,997, dated Dec. 11, 2012, 9 pages.
Final Office Action received for U.S. Appl. No. 12/611,997, dated Nov. 10, 2011, 15 pages.
Final Office Action received for U.S. Appl. No. 13/049,199, dated Apr. 4, 2012, 10 pages.
Final Office Action received for U.S. Appl. No. 13/207,381, dated Nov. 2, 2012, 7 pages.
Final Office Action received for U.S. Appl. No. 14/271,342 dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 12/611,997, dated Oct. 24, 2013, 10 pages.
Final Office Action received for U.S. Appl. No. 13/049,199 dated Aug. 11, 2014, 8 pages.
Final Office Action received for U.S. Appl. No. 13/207,381, dated Nov. 7, 2013, 7 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107 dated Sep. 1, 2015, 9 pages.
Final Office Action received for U.S. Appl. No. 13/646,570, dated Dec. 23, 2014, 10 pages.
Final Office Action received for U.S. Appl. No. 14/229,735, dated Aug. 27, 2015, 7 pages.
Final Office Action received for U.S. Appl. No. 14/273,063, dated Dec. 28, 2016, 11 pages.
Final Office Action received for U.S. Appl. No. 14/660,539, dated Aug. 3, 2017, 11 pages.
Gambihler et al., "Permeabilization of the Plasma Membrane of LI210 Mouse Leukemia Cells Using Lithotripter Shock Waves", The Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep vol. 14, 2012, pp. 567-572.
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2009/063354, dated May 19, 2011, 6 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2012/063925, dated May 22, 2014, 12 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987, dated Nov. 20, 2014, 11 pages.
International Preliminary Report on Patentability received for PCT Patent Application No. PCT/US2013/048277, dated Jan. 8, 2015, 9 pages.
International Preliminary Report on Patentability received for PCT Patent Application No. PCT/US2013/055431, dated Feb. 26, 2015, 7 pages.
International Preliminary Report on Patentability received for PCT Patent Application No. PCT/US2013/059533 dated Mar. 26, 2015, 10 pages.
International Preliminary Report on Patentability received for PCT Patent Application No. PCT/US2015/029088, dated Nov. 17, 2016, 8 pages.
International Search Report and Written Opinion received for PCT Application No. PCT/US2018/034855, dated Aug. 23, 2018, 13 pages.
International Search Report and Written Opinion received for PCT Patent Application No. PCT/US2013/031805 dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.

(56) References Cited

OTHER PUBLICATIONS

International Search Report and Written Opinion received for PCT Patent Application No. PCT/US2013/059533, dated Nov. 7, 2013, 14 pages.
International Search Report and Written Opinion received for PCT Patent Application No. PCT/US2015/029088, dated Jul. 16, 2015, 13 pages.
International Search Report and Written Opinion received for PCT Patent Application No. PCT/US2016/060817, dated Feb. 20, 2017, 13 pages.
International Search Report and Written Opinion received for PCT Patent Application No. PCT/US2019/035750, dated Aug. 1, 2019, 21 pages.
International Search Report received for PCT Patent Application No. PCT/US2009/047070, dated Jan. 19, 2010, 4 pages.
International Search Report received for PCT Patent Application No. PCT/US2009/063354, dated Jun. 11, 2010, 3 pages.
International Search Report received for PCT Patent Application No. PCT/US2012/023172, dated Sep. 28, 2012, 3 pages.
International Written Opinion received for PCT Patent Application No. PCT/US2009/063354, dated Jun. 11, 2010, 4 pages.
International Written Opinion received for PCT Patent Application No. PCT/US2011/047070, dated May 1, 2012, 5 pages.
Kodama et al., "Shock Wave-mediated Molecular Delivery into Cells", Biochimica et Biophysica Acta vol. 1542, 2002, pp. 186-194.
Lauer et al., "Shock Wave Permeabilization as a New Gene Transfer Method", Gene Therapy vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 12/611,997, dated Nov. 26, 2014, 8 pages.
Non-Final Office Action received for U.S. Appl. No. 13/207,381, dated Nov. 25, 2014, 5 pages.
Non-Final Office Action received for U.S. Appl. No. 13/465,264, dated Oct. 29, 2014, 13 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 12/482,995, dated Feb. 11, 2011, 27 pages.
Non-Final Office Action received for U.S. Appl. No. 12/501,619, dated Jan. 28, 2014, 10 pages.
Non-Final Office Action received for U.S. Appl. No. 12/501,619, dated Nov. 3, 2011, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 12/611,997, dated Apr. 8, 2013, 9 pages.
Non-Final Office Action received for U.S. Appl. No. 12/611,997, dated Aug. 24, 2012, 11 pages.
Non-Final Office Action received for U.S. Appl. No. 12/611,997, dated Feb. 13, 2014, 9 pages.
Non-Final Office Action received for U.S. Appl. No. 12/611,997, dated Jun. 21, 2011, 13 pages.
Non-Final Office Action received for U.S. Appl. No. 13/049,199, dated Dec. 12, 2011, 10 pages.
Non-Final Office Action received for U.S. Appl. No. 13/049,199, dated Feb. 4, 2014, 8 pages.
Non-Final Office Action received for U.S. Appl. No. 13/207,381, dated Feb. 22, 2013, 7 pages.
Non-Final Office Action received for U.S. Appl. No. 13/207,381, dated Feb. 25, 2014, 8 pages.
Non-Final Office Action received for U.S. Appl. No. 13/207,381, dated Jun. 12, 2012, 6 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/534,658, dated Mar. 11, 2016, 12 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/218,858, dated Mar. 30, 2016, 13 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 14/273,063, dated Jun. 3, 2016, 9 pages.
Non-Final Office Action received for U.S. Appl. No. 14/515,130, dated Jan. 14, 2016, 16 pages.
Non-Final Office Action received for U.S. Appl. No. 14/660,539, dated Nov. 24, 2017, 10 pages.
Non-Final Office Action received for U.S. Appl. No. 14/693,155, dated Jan. 15, 2016, 6 pages.
Non-Final Office Action received for U.S. Appl. No. 15/474,885, dated Oct. 5, 2017, 9 pages.
Non-Final Office Action received for U.S. Appl. No. 15/652,070, dated Jan. 11, 2019, 9 pages.
Non-Final Office Action received for U.S. Appl. No. 14/660,539, dated Mar. 6, 2017, 14 pages.
Notice of Acceptance received for Australian Patent Application No. 2009257368, dated Aug. 28, 2014, 2 pages.
Notice of Acceptance received for Australian Patent Application No. 2009313507, dated Nov. 17, 2014, 2 pages.
Notice of Allowance received for Canadian Patent Application No. 2,727,429, dated May 26, 2015, 1 page.
Notice of Allowance received for Canadian Patent Application No. 2,779,600, dated Jul. 7, 2017, 1 page.
Notice of Allowance received for Chinese Patent Application No. 201380033808.3, dated Dec. 29, 2016, 4 pages (Official copy only) (See Communication under 37 CFR § 1.98(a) (3)).
Notice of Allowance received for Chinese Patent Application No. 201380041656.1, dated Mar. 3, 2017, 4 pages (Official copy only) (See Communication under 37 CFR § 1.98(a) (3)).
Notice of Allowance received for Japanese Patent Application No. 2015-036444, dated Jan. 13, 2017, 3 pages (Official copy only) (See Communication under 37 CFR § 1.98(a) (3)).
Notice of Allowance received for Japanese Patent Application No. 2015-520522, dated Feb. 23, 2017, 3 pages (Official copy only) (See Communication under 37 CFR § 1.98(a) (3)).
Notice of Allowance received for U.S. Appl. No. 15/652,070, dated May 21, 2019, 8 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 12/611,997, dated Apr. 15, 2015, 7 pages.
Notice of Allowance received for U.S. Appl. No. 13/207,381, dated Apr. 14, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.

(56) References Cited

OTHER PUBLICATIONS

Notice of Allowance received for U.S. Appl. No. 13/049,199, dated Jan. 13, 2015, 4 pages.
Notice of Allowance received for U.S. Appl. No. 13/534,658, dated Jan. 5, 2017, 6 pages.
Notice of Allowance received for U.S. Appl. No. 13/534,658, dated Jan. 18, 2017, 4 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 14/273,063, dated Apr. 12, 2017., 7 pages.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 14/660,539, dated Apr. 6, 2018, 7 pages.
Notice of Allowance received for U.S. Appl. No. 14/693,155, dated Apr. 26, 2016, 9 pages.
Notice of Allowance received for U.S. Appl. No. 15/474,885, dated Feb. 14, 2018, 5 pages.
Notice of Allowance received for U.S. Appl. No. 13/615,107, dated Dec. 31, 2015, 10 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Australian Patent Application No. 2009313507, dated Nov. 13, 2013, 3 pages.
Office Action received for Australian Patent Application No. 2013284490, dated Jun. 5, 2017, 4 pages.
Office Action received for Australian Patent Application No. 2013300176, dated Nov. 10, 2016, 2 pages.
Office Action received for Canadian Patent Application No. 2,727,429, dated Apr. 14, 2015, 4 pages.
Office Action received for Canadian Patent Application No. 2,779,600, dated Jan. 4, 2016, 6 pages.
Office Action received for Canadian Patent Application No. 2,779,600, dated Oct. 19, 2016, 3 pages.
Office Action received for Chinese Patent Application No. 200980153687.x, dated Dec. 26, 2012, 11 pages (Official copy only) (See Communication under 37 CFR § 1.98(a) (3)).
Office Action received for Chinese Patent Application No. 200980153687.x, dated Jul. 11, 2013, 11 pages (Official copy only) (See Communication under 37 CFR § 1.98(a) (3)).
Office Action received for Chinese Patent Application No. 201380033808.3, dated Jul. 5, 2016., 9 pages (3 pages of English Translation and 6 pages of Official copy).
Office Action received for Chinese Patent Application No. 201380041656.1, dated Jul. 5, 2016., 9 pages (4 pages of English Translation and 5 pages of Official copy).
Office Action received for Chinese Patent Application No. 201380042887.4, dated Aug. 8, 2016, 9 pages (4 pages of English Translation and 5 pages of Official copy).
Office Action received for European Patent Application No. 09763640.1, dated Dec. 2, 2016, 4 pages.
Office Action received for Japanese Patent Application No. 2011-513694, dated Aug. 27, 2013, 6 pages (3 pages of English Translation and 3 pages of Official copy).
Office Action received for Japanese Patent Application No. 2011-513694, dated Jun. 10, 2014, 4 pages total (2 pages of Official copy and 2 pages of English Translation).
Office Action received for Japanese Patent Application No. 2011-534914, dated Jan. 13, 2015, 9 pages(7 pages of English Translation and 2 pages of Official copy.
Office Action received for Japanese Patent Application No. 2011-534914, dated Jul. 15, 2014, 3 pages (1 page of English Translation and 2 pages of Official copy).
Office Action received for Japanese Patent Application No. 2011-534914, dated May 10, 2016, 10 pages (4 pages of Official copy and 6 pages of English Translation).
Office Action received for Japanese Patent Application No. 2011-534914, dated Oct. 1, 2013, 5 pages (2 pages of English Translation and 3 pages of Official copy).
Office Action received for Japanese Patent Application No. 2014-158517, dated Feb. 15, 2017, 8 pages (5 pages of English Translation and 3 pages of Official copy).
Office Action received for Japanese Patent Application No. 2014-158517, dated Jun. 22, 2017., 14 pages (Official copy only) (See Communication under 37 CFR § 1.98(a) (3)).
Office Action received for Japanese Patent Application No. 2014-158517, dated May 19, 2015, 5 pages (2 pages of English Translation and 3 pages of Official copy).
Office Action received for Japanese Patent Application No. 2015-036444, dated Feb. 23, 2016, 3 pages of English Translation only.
Office Action received for Japanese Patent Application No. 2015-526523, dated Jan. 25, 2017, 8 pages (5 pages of English Translation and 3 pages of Official copy).
Office Action received for Japanese Patent Application No. 2016-143049, dated Apr. 24, 2017., 5 pages (2 pages of English Translation and 3 pages of Official copy).
Office Action received for Japanese Patent Application No. 2015-036444, dated Sep. 14, 2016, 5 pages (3 pages of English Translation and 2 pages of Official copy).
Office Action received for Japanese Patent Application No. 2016-094326, dated Dec. 2, 2016, 4 pages (2 pages of English Translation and 2 pages Official copy).
Office Action received for Japanese Patent Application No. 2016-094326, dated Jul. 6, 2017, 2 pages (Official copy only) (See Communication under 37 CFR § 1.98(a) (3)).
Rosenschein et al., "Shock-wave Thrombus Ablation, a New Method for Noninvasive Mechanical Thrombolysis", The American Journal of Cardiology, vol. 70, Nov. 15, 1992, pp. 1358-1361.
Sakes et al., "Crossing Total Occlusions: Navigating Towards Recanalization", Cardiovascular Engineering and Technology, vol. 7, No. 2, Jun. 2016, pp. 103-117.
Written Opinion received for PCT Patent Application No. PCT/US2012/023172, dated Sep. 28, 2012, 4 pages.
Written Opinion received for PCT Patent Application No. PCT/US2009/047070, dated Jan. 19, 2010, 5 pages.
Zhong et al., "Transient Oscillation of Cavitation Bubbles Near Stone Surface During Electrohydraulic Lithotripsy", Journal of Endourology, vol. 11, No. 1, Feb. 1997, pp. 55-61.
International Preliminary Report on Patentability received for PCT Patent Application No. PCT/US2019/035750, dated Dec. 30, 2020, 11 pages.
International Search Report and Written Opinion received for PCT Patent Application No. PCT/US2020/051551, dated Jan. 11, 2021, 16 pages.
U.S. Appl. No. 17/025,866, filed Sep. 18, 2020, titled "System for Treating Thrombus in Body Lumens," (Copy not submitted herewith pursuant to the waiver of 37 C.F.R. § 1.98(a)(2)(iii)).
International Search Report and Written Opinion received for PCT Patent Application No. PCT/US2021/071938 dated Jan. 18, 2022, 13 pages.

\* cited by examiner
† cited by third party

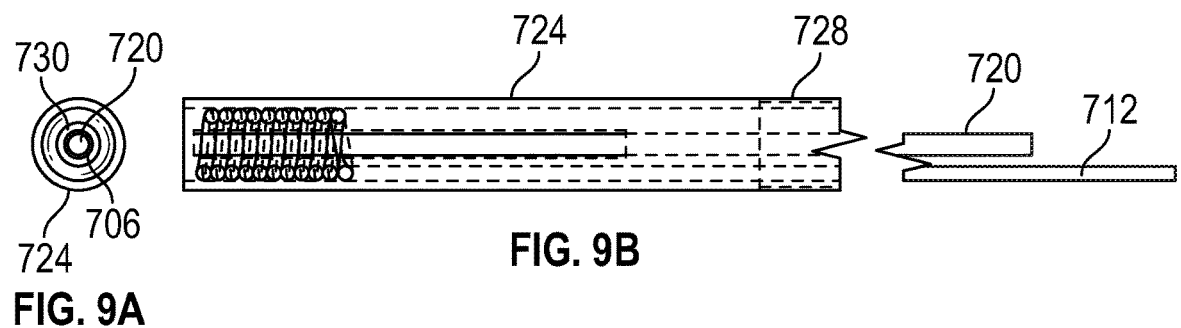
FIG. 9A
FIG. 9B
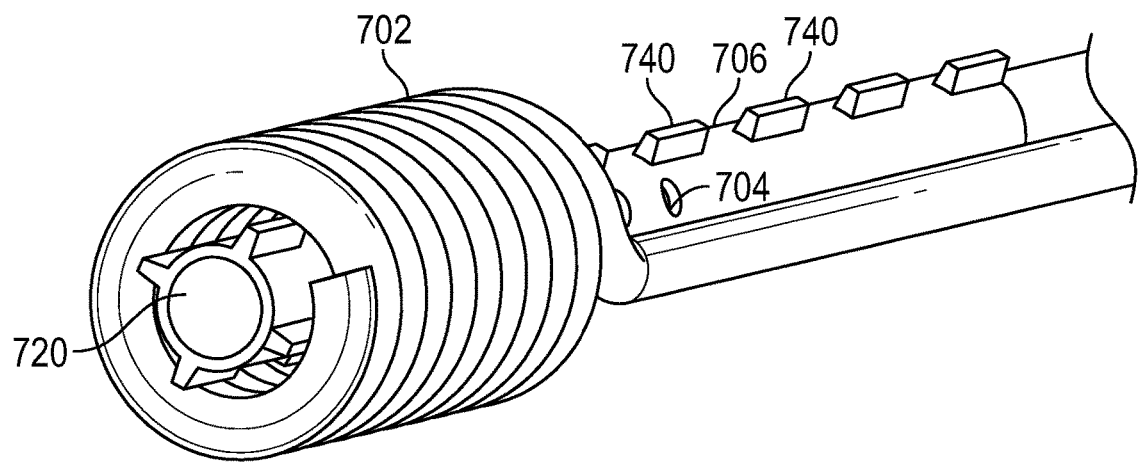
FIG. 10

SYSTEM FOR TREATING OCCLUSIONS IN BODY LUMENS

PRIORITY

This application claims priority to U.S. Patent Application Ser. No. 62/688,110 filed Jun. 21, 2018, the entire disclosure of which is incorporated herein by reference.

BACKGROUND

The present disclosure relates generally to a system for treating occlusions in a body lumen. The system is useful for a chronic total coronary occlusion ("CTO"), a partial coronary occlusion, or a kidney stone in ureter, in order to restore normal flow in a lumen (e.g., the artery or the ureter).

In angioplasty or peripheral angioplasty procedures, an angioplasty balloon is used to dilate a lesion (e.g., calcified lesion) and restore normal blood flow in the artery. In some examples, an angioplasty balloon is advanced into the vasculature (e.g., along a guide wire) until the balloon is aligned with calcified plaques. The balloon is then pressurized with a fluid to expand the vessel to permit blood flow.

More recently, a system has been developed wherein electrodes are disposed in the angioplasty balloon. Once the balloon is initially positioned adjacent a blockage, a series of high voltage pulses are applied to the electrodes in a manner to generate a series of shock waves. The shock waves act to crack calcified lesions. Once the lesions are cracked, the balloon can be inflated, in a more gentle fashion, to expand the vessel and improve circulation.

Further information about the latter type of device can be found in U.S. Pat. Nos. 8,856,371; 8,747,416 and 9,642,673. Shock wave technology has also been developed for treating heart valves (U.S. 2018/0098779) and for guide wire designs (U.S. Pat. No. 9,730,715). U.S. Patent Publication 2018/03640482 describes a forward directed shock wave device. Each of these patent documents is incorporated herein by reference.

Arteries are sometimes totally or partially occluded, for example, with thrombus, plaque, fibrous plaque, and/or calcium deposits. When this condition is present, the physician must first cross the occlusion, and then feed the angioplasty balloon and/or other tools down the artery to the desired location of blockage to perform the desired procedure. However, in some instances (e.g., CTO), the occlusion is so tight and solid, making it difficult to cross the treatment device into the true lumen of the distal vessel.

CTOs remain a challenge in percutaneous coronary interventions, as well as a challenge for the periphery, causing critical limb ischemia and amputations. First, many of the currently available equipment are incapable of physically crossing the tough proximal cap or distal cap (retrograde approach) of the CTO. In some instances, attempting to penetrate the CTO cap using soft guide wire causes buckling (e.g., deflecting the guidewire to a subintimal passage or collateral branch). On the other hand, stiffer guide wires may damage the artery wall when forced against the CTO. Moreover, some currently available equipment operate by generating strong mechanical vibrations to break the CTO, but the intensity of the vibration may damage the artery wall and make the system less durable and more difficult to control.

Similar issues are present for occlusions formed in other parts of the body, for example, kidney stones in a ureter.

BRIEF SUMMARY

The invention provides a system for treating an occlusion such as CTO or kidney stones within a lumen such as a blood vessel or a ureter. In some embodiments, the system comprises an insulated outer sheath, an elongated conductive tube, wherein the insulated outer sheath is circumferentially mounted around the elongated conductive tube, and an insulated wire having a helically coiled portion at a distal end of the insulated wire. The coiled portion includes an exposed distal tip. A distal portion of the elongated conductive tube is circumferentially mounted around the distal coiled portion of the insulated wire. When a voltage is applied across the insulated wire and the elongated conductive tube, a current is configured to flow from the exposed distal tip of the insulated wire to the elongated conductive tube to ionize the fluid around it and generate a plurality of cavitation bubbles and bubble-associated dynamics (collapses, jets, etc.).

In some embodiments, a method for treating an occlusion within a lumen such as a blood vessel or a ureter comprises advancing a treatment device within the lumen to contact the occlusion. The treatment device comprises: an insulated outer sheath; an elongated conductive tube, wherein the insulated outer sheath is circumferentially mounted around the elongated conductive tube; and an insulated wire having a helically coiled portion at a distal end of the insulated wire, wherein the coiled portion includes an exposed distal tip and wherein a distal portion of the elongated conductive tube is circumferentially mounted around the distal coiled portion of the insulated wire. The method further comprises injecting conductive fluid (i.e. physiological saline, mixture of saline and angiographic contrast dyes, etc.) toward a distal end of the treatment device; and applying a voltage across the insulated wire and the elongated conductive tube to cause a current to flow from the exposed distal tip of the insulated wire to the elongated conductive tube to generate a plurality of cavitation bubbles and bubble-associated dynamics (collapses, jets, etc.).

In some embodiments, a system for treating an occlusion within a body lumen is disclosed. The system includes an insulated wire having a helically coiled portion near the distal end thereof, and with the distal tip of the insulated wire having a portion of the insulation removed to define an electrode. The system further includes an elongated central electrode with the distal end thereof being received within the helically coiled portion of the insulated wire. In one preferred embodiment, the system further includes an insulated tube located about the distal end of the central electrode and within the helically coiled portion of the insulated wire. Finally, a tubular outer shell is provided for covering the coiled portion of the insulated wire. The proximal ends of the insulated wire and the central electrode are connectable to the terminals of an electrical pulse generator so that in use, when voltage pulses are applied to the central electrode and the insulated wire, a series of cavitation bubbles are created between the electrode of the insulated wire and the central electrode.

DESCRIPTION OF THE FIGURES

FIG. 9A is an end view of the system of FIG. 7.

FIG. 9B is a cross-sectional view of the system of FIG. 7.

FIG. 10 is a perspective view of a bubble generating tip system of another exemplary in accordance with some embodiments.

DETAILED DESCRIPTION

The following description sets forth exemplary methods, parameters, and the like. It should be recognized, however, that such description is not intended as a limitation on the scope of the present disclosure but is instead provided as a description of exemplary embodiments.

Described herein are exemplary systems and methods for treating an occlusion such as CTO or kidney stones in a ureter. In according with some embodiments, the treatment system includes a forward bubble generating tip to be advanced within the lumen to contact the occlusion. The forward bubble generating tip includes electrodes that, when provided with a relatively low-voltage and high-PRF (pulse repetition rate) generator, form plasma arcs that in turn lead to cavitation bubbles. The cavitation bubbles create mechanical vibrations, turbulence, jets, and/or forceful collapses to break the occlusion. The output of the generator is configured to be sufficient for creating electro-hydraulic discharge and cavitation bubbles for effectively drilling, but not enough to create a powerful shock wave that may compromise the durability of the system. As such, the mechanical vibrations are relatively gentle compared to currently available equipment. Accordingly, the treatment system is less likely to cause damage to the lumen wall (e.g., vessel wall) and is easier to control and more durable.

Figure 1:
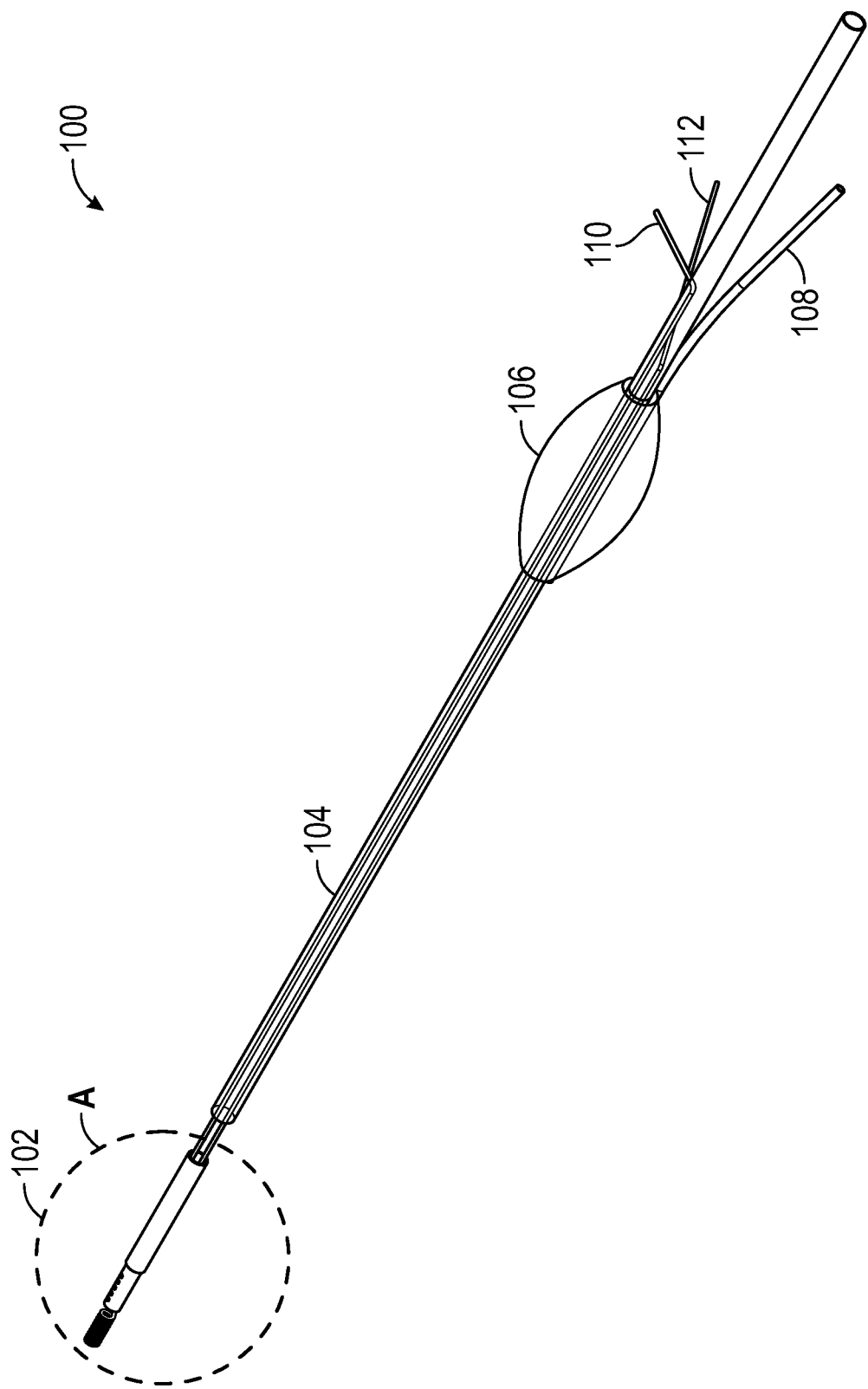
FIG. 1 is a perspective view of an exemplary system for treating an occlusion, in accordance with some embodiments.

FIG. 1 is a perspective view of an exemplary treatment system 100 in accordance with some embodiments. The treatment system includes a forward bubble generating tip 102 (shown in an expanded view), an insulated outer sheath 104, a proximal balloon 106 mounted over a length of the insulated outer sheath, a waste conduit 108, and insulated wires 110 and 112. The forward bubble generating tip 102 includes electrodes and is described in detail with reference to FIGS. 2A-C. In operation, conductive fluid such as saline (or saline contrast mix) is injected from the proximal opening of the insulated outer sheath 104 and flows toward the distal end. When the proximal ends of the insulated wires 110 and 112 are connected to a voltage supply, cavitation bubbles and/or shock waves are generated via the conductive fluid at the forward bubble generating tip. The cavitation bubbles and/or shock waves lead to sustained mechanical vibrations in the forward direction, breaking down the occlusion such as CTO or kidney stones. As more conductive fluid is injected, debris such as broken down occlusion pieces, metals, and bubbles are flushed toward the proximal balloon and carried out of the lumen via the waste conduit 108.

Figure 2A:
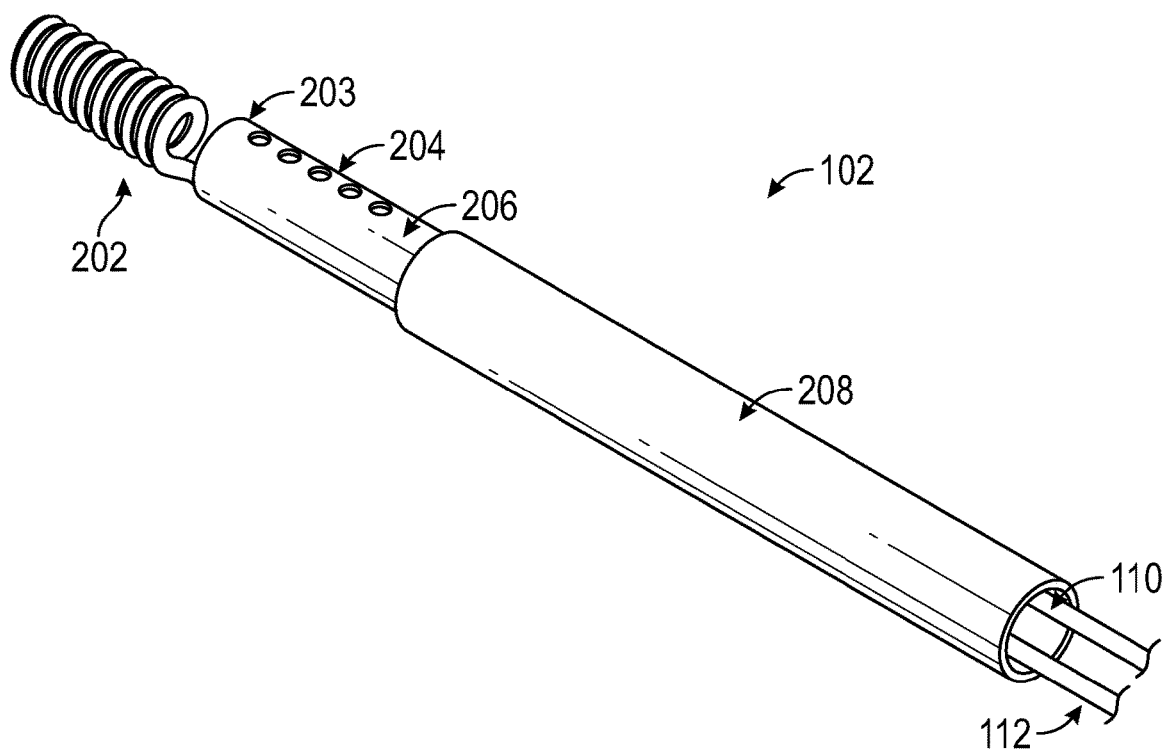
FIG. 2A is an expanded view of an exemplary bubble generating tip of the treatment system, in accordance with some embodiments.

FIG. 2A depicts an expanded view of the forward bubble generating tip 102 of FIG. 1. As depicted, the forward bubble generating tip 102 includes an elongated conductive tube 208, a helically coiled portion 202 at the distal end of the insulated wire 112, and an optional insulated layer 206 disposed between the elongated conductive tube 208 and the helically coiled portion 202. In the depicted example, the insulated layer 206 includes a plurality of holes 204 arranged along the longitudinal axis. In some examples, the elongated conductive tube 208 can be a stainless steel hypotube. The insulated wires 110 and 112 can be polyimide-insulated copper wires. The insulated layer 206 can be a polyimide tubular insulator. The insulated layer provides an extra layer of insulation between the conductive core of wire 112 and the elongated conductive tube 208 and is helpful in case the insulation around the coiled portion 202 has defects and/or experiences damages (e.g., scratching during assembly). In some examples, the forward bubble generating tip 102 does not include the insulated layer 206. In some examples, epoxy or cyano glue can be used between the coiled portion 202 and the elongated conductive tube 208 to fix the relative positioning of the two.

Figure 2B:
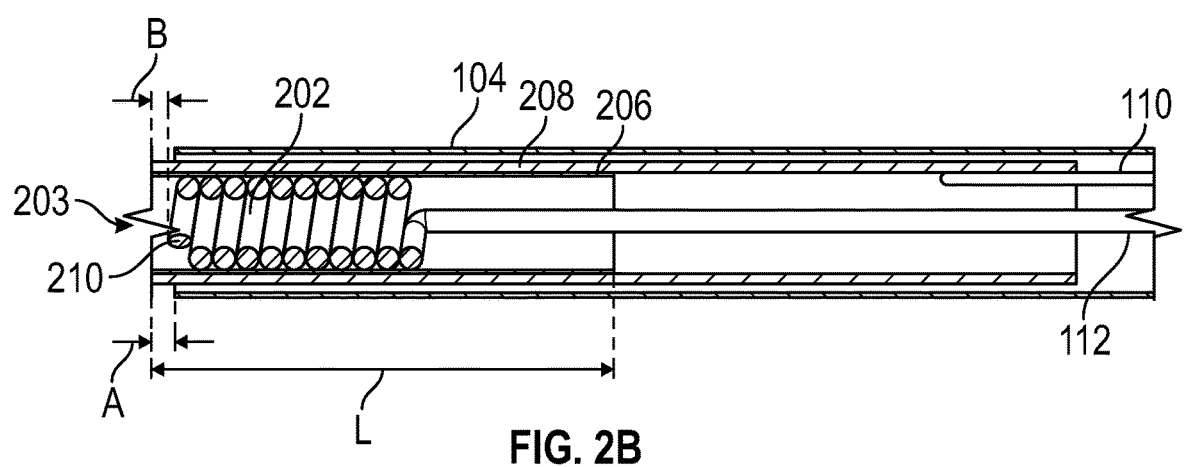
FIG. 2B is a cross-sectional view of an exemplary bubble generating tip of the treatment system, in accordance with some embodiments.

FIG. 2B depicts a cross-sectional view of the forward bubble generating tip 102. As depicted, the insulated outer sheath 104 is circumferentially mounted over the elongated conductive tube 208. In the depicted example, the distal edge of the elongated conductive tube 208 extends over distal edge of the insulated outer sheath 104 by distance A. The distance A can be adjusted based on the characteristics of the occlusion. For example, the distance A can be set to be longer than the thickness of the calcified cap of the CTO to be drilled through. If not, the crossing profile would need to be undesirably increased (i.e. a bigger hole needs to be drilled to accommodate the insulated outer sheath). In some examples, the distance A ranges from 0.004" to 0.01". As further depicted, an insulated layer 206 is disposed, for a longitudinal length of L, between the elongated conductive tube 208 and the helically coiled wire portion 202. The distal end of the insulated wire 110 is welded to the elongated conductive tube 208.

As depicted, the distal edge of the insulated layer 206 is aligned with the distal edge of the elongated conductive tube 208. Further, the distal edge of the elongated conductive tube 208 extends beyond the helically coiled wire portion 202 by distance B. In some examples, the distance B ranges from 0 mm (i.e., the distal end of the coiled portion is aligned with the distal edge of the elongated tube) to 0.5 mm. In some examples, one or more of the other factors that affect the efficiency of the operation, such as the flow rate of the conductive fluid, the applied voltage, the shape and composition of the occlusion, are taken into account when setting distance B to achieve an optimal configuration. This relative positioning of the helically coiled wire portion 202 and the distal edges of the insulated layer 206 and elongated conductive tube 208 ensures safety to the surrounding tissue, protects the catheter from the vibrations emitting from the tip, and causes the mechanical vibrations to be generated in a forward-facing direction, thus increasing the intensity, and thus the effectiveness, of the treatment system in breaking down the occlusion. Further, the forward-facing mechanical vibrations, along with the continuous flow rate in the forward direction, result in drilling of holes that are consistent (e.g., in size, in shape), thus making the treatment system easier to operate. In some examples, the treatment system is configured to drill holes of around 1 mm in diameter in calcified materials.

In some examples, the flow of saline or saline/angiographic contrast mix is adjusted to avoid over-heating issues and control drilling efficiency and rate. In some examples, the flow rate is configured to be in the range of 1 to 30 mL/min to improve breakability of calcified structures.

In an exemplary operation, when the proximal ends of the insulated wires 110 and 112 are connected to the negative port and positive port of a generator, respectively, a current flows from the distal end 210 of the insulated wire 112 to the elongated conductive tube 208. The current can cause a plurality of plasma arcs to be formed between the distal end 210 of the insulated wire 112 and the inner diameter of the elongated conductive tube 208 (e.g., across the distal edge 203 of the insulated layer 206 or through the holes 204 in 206). The plasma arcs lead to cavitation bubbles in a controlled fashion (one at a time, at a particular rate), which in turn lead to mechanical vibrations, and other bubble dynamics-related effects such as collapses, turbulence, jetting, etc. in the conductive fluid (e.g., via the expansion and collapse of the bubbles). The mechanical vibrations serve to break or chip away the occlusion. As compared to the generators used in the prior art shock wave generation systems mentioned above, the generator for this system is configured to generate lower-voltage pulses at a higher pulse repetition rate in order to minimize the strength of the shock waves and optimize and maximize bubble growth and collapse. For example, in the prior art systems, each pulse might be about 3000 volts with a 1 Hz repetition rate. In this system, the voltage can be under 1000 volts with the repetition rates ranging from 14 to 200 Hz. In a preferred embodiment, repetition rates can as high as 800 Hz.

As the plasma arcs cause erosion to the electrodes in operation, the helically coiled wire portion 202 and/or the insulation over the coiled wire portion can disintegrate and shorten over time. Similarly, the insulation layer 206 and the distal edge of the elongated conductive tube 208 can disintegrate due to use. The rates at which the coiled wire portion, the insulated layer, and the elongated conductive tube disintegrate can vary based on physical characteristics of each component (e.g., the diameter of the wire, the property of the wire, the thickness of the insulation layer), the polarities of the applied voltage, the magnitude of the applied voltage, etc. For example, a wire that is relatively thin, connected to a relatively high voltage supply, and/or connected to the positive voltage port would erode faster. In some instances, before the helically coiled wire portion 202 experiences extensive usage, the plasma arcs are generated across the distal edge 203 of the insulated layer 206. However, as the helically coiled wire portion 202 shortens due to usage, the distance between the distal end 210 of the insulated wire 112 and the distal edge of the insulated layer 206 increases. Due to the increased distance, plasma arcs are no longer generated across the distal edge 203 of the insulated layer 206. Instead, as current flows from the distal end 210 of the helically coiled wire portion 202 to inner diameter of the elongated conductive tube 208, plasma arcs are generated across one of the holes 204 (e.g., the hole located closest to the distal end 210 of the shortened helically coiled wire portion) in the insulated layer 206. As shown in FIG. 2A, a plurality of holes are provided along the longitudinal axis of the insulated layer 206, thus allowing plasma arcs to be formed even as the helically coiled wire portion 202 shortens and improving the durability of the treatment system. In other words, the holes in the conductive layer aim to become new spark areas as the device (i.e., the electrodes) erodes. In some examples, the plurality of holes is arranged in a spiral orientation to be aligned with the coil to control the maximum arc length. In some examples, the applied voltage is sustained for a relatively long periods of time (e.g., minutes) to achieve continuous generation of cavitation bubbles and eventual crossing. Note that as the coiled wire portion erodes, the location of the generation of the cavitation bubbles will change. In the illustrated embodiment, the location of the generation of the cavity bubbles will rotate circumferentially about the periphery of the conductive tube 208.

In some examples, various parameters can be adjusted during the operation to slow down or even out the erosion of the electrodes. For example, the frequency of bubble generation/emission (pulses per minute) can be adjusted to control the tip erosion, durability and drilling time. The frequency of bubble generation can be controlled by reducing the capacitance (so a capacitance switch can change the speed on demand), or by reducing the current power supply. As another example, the applied voltage can be adjusted as a function of drilling time to control the emitter erosion and device durability while maintaining the frequency constant as a function of drilling time. Further, polarity of the electrodes can be reversed for a period of time equivalent to a fraction of the treatment time (e.g., 10% to 100% of the time) while maintaining the voltage and frequency constant as a function of drilling time in order to control electrode wear and improve device durability. Further still, the thickness of the wire insulation can be chosen to control the durability of the wire.

U.S. Pat. No. 10,226,265, incorporated by reference, teaches various approaches for switching polarity of electrode pairs positioned in a conductive fluid. Those types of approaches can be utilized with the subject device. In particular, to maintain peak sonic output, the spark gap should be constant. As the electrodes erode away, the gap can vary. To compensate for this variation in gap size, the polarity on the electrodes can be reversed. The polarity reversal frequency can be used to help control variations in the length of the spark gap. It is possible to tune the polarity reversal frequency based on the power being delivered, wire diameter and insulator thickness. It is also possible to have the generator detect the power degradation and automatically reverse the polarity on the electrodes.

Figure 2C:
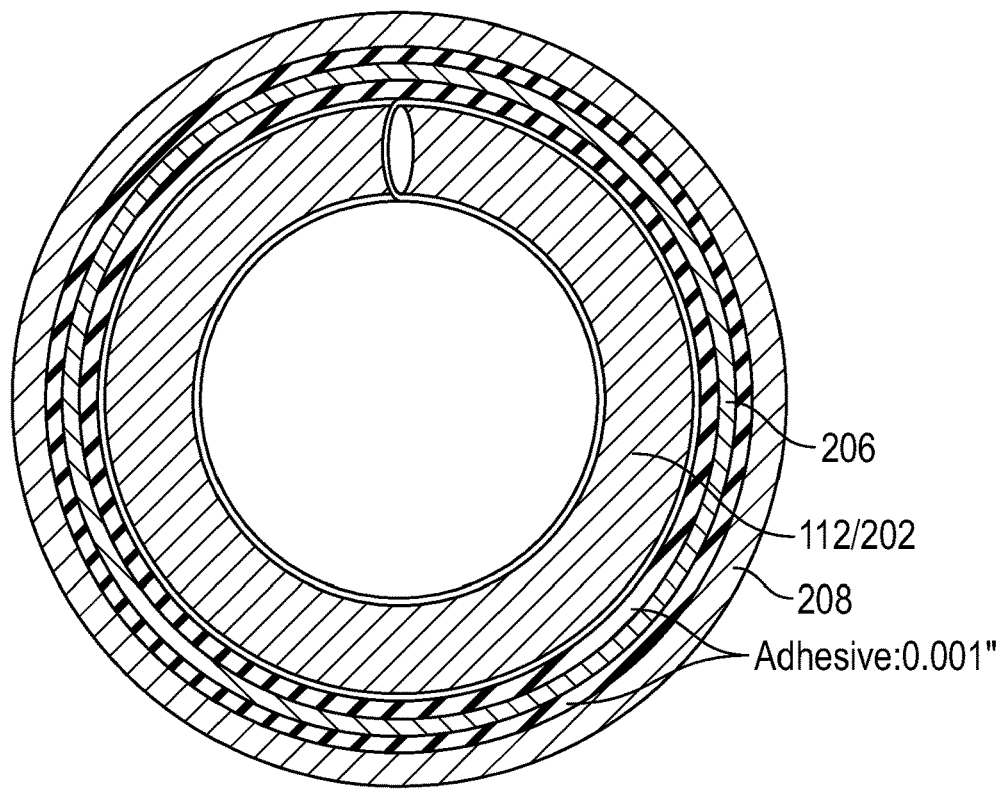
FIG. 2C is a cross-sectional view of an exemplary bubble generating tip of the treatment system, in accordance with some embodiments.

FIG. 2C is a cross-sectional view of an exemplary bubble generating tip of the treatment system, in accordance with some embodiments. The insulated wire 112 has a typical diameter of 0.005" in the core (e.g., copper core) with 0.0005" polyimide coating. The number of turns of the coiled wire portion dictates the life of the electrode. With ~500V-700V arcing at 100 Hz, one turn can last approximately 30-40 seconds. Thus, for a 10-minute procedure, the coiled wire portion can include around 17 turns and the coil length would be around 0.1". The length of the elongated conductive tube 208 should be longer than the coil length to support internal features. The insulated layer 206 (e.g., polyimide insulator sheath) can have a thickness of 0.001". The outer diameter of the insulated layer 206 is fitted inside the inner diameter of the elongated conductive tube 208. The outer diameter of the elongated conductive tube 208 (e.g., stainless steel hypotube) can range between 0.035" to 0.065" with the thickness of 0.002". Arcing gap between the wire core (e.g., copper core) and the inner diameter of the elongated conductive tube is around 0.004"-0.007". The arc gap could be longer if the insulting layer 206 and a hole 204 is further away, for example the other side of the tube. In some examples, the arcing gap is the ideal range to maximize the cavitation. In some examples, the various dimensions of the system are selected to be compatible with off-shelf components.

Figure 3:
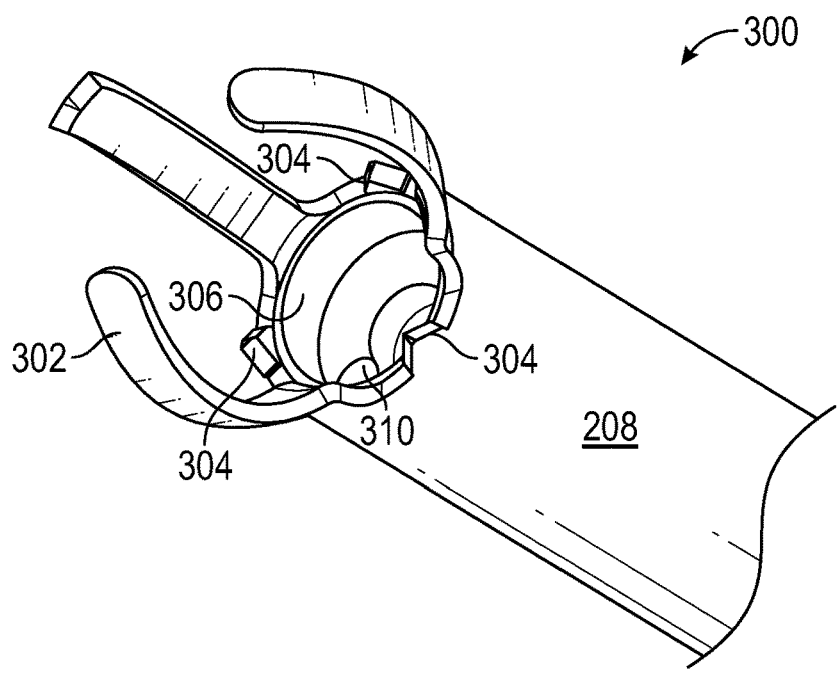
FIG. 3 is a perspective view of another exemplary bubble generating tip of the treatment system, in accordance with some embodiments.

FIG. 3 depicts a perspective view of an alternative forward bubble generating tip 300 of the treatment system, in accordance with some embodiments. The forward bubble generating tip 300 includes a plurality of atraumatic arms or tines 302 extending from the distal end of the elongated conductive tube 208. The tines 302 are made of flexible materials and are designed to deflect the tip from perforating the lumen wall. In some examples, the tines can be coated with elastomer (i.e., silicone rubber) or low durometer polymer (i.e., polyurethane), and can be around 0.035" in length. When the forward bubble generating tip drills a hole through the occlusion and gets to soft tissue, the flexible tines cause the tip to turn. Further, the forward bubble generating tip 300 includes a plurality of spikes 304 extending from the distal end of the elongated conductive tube 208. The spikes 304 are designed to direct the plasma arcs between the distal end 310 of the coiled wire portion and the distal edge of the elongated conductive tube 208, for example, across the distal edge of the insulated layer 306.

Figure 4:
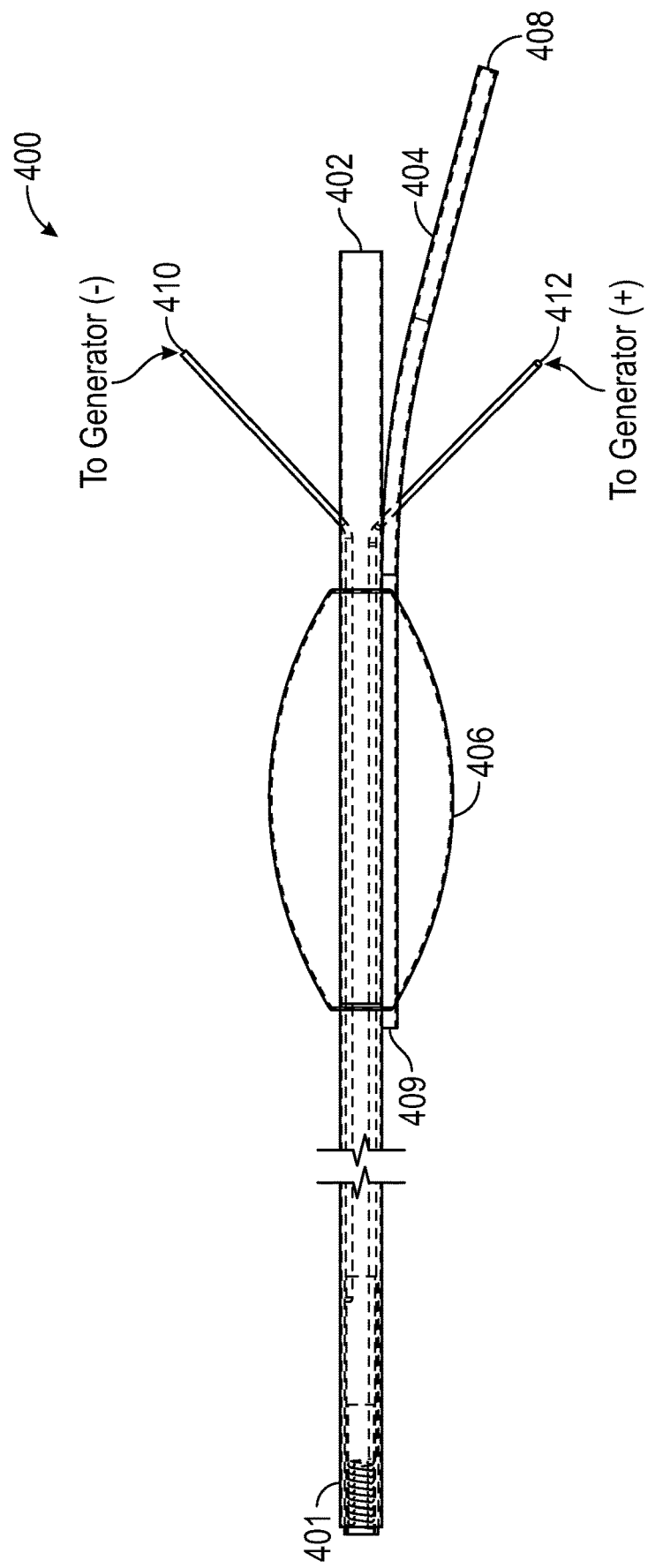
FIG. 4 is a side view of an exemplary system for treating an occlusion, in accordance with some embodiments.

FIG. 4 is a side view of an exemplary system 400 for treating an occlusion, in accordance with some embodiments. As depicted, the proximal end of the insulated outer sheath forms an inlet 402 for injecting conductive fluid (e.g., saline). This port 402 could also act as a conduit to introduce a guidewire (e.g., a 0.014" guidewire) after flushing or while flushing the saline. The injected conductive fluid serves a number of purposes. First, when the proximal ends of wires 410 and 412 are connected to a voltage supply, plasma arcs can be formed via the conductive fluid at the forward bubble generating tip, as described above with reference to FIGS. 1-3. Further, continually injecting conductive fluid helps to dissipate heat and cool the electrodes. Flow also creates forward inertia to help the bubbles to drill and collapse (and jet) forward. In some example, the flow rate is adjusted to control the drilling efficiency and rate. Moreover, the conductive fluid flushes through the coiled wire portion at the forward bubble generating tip and carries the debris such as broken down occlusion pieces, metals, and bubbles away from the forward bubble generating tip 401 toward the proximal balloon 406. The proximal balloon, when inflated, traps the debris and prevents the debris from entering the main artery. As depicted, a conduit 404 extends through the proximal balloon 406, and the distal end 409 of the conduit 404 serves as a waste inlet for receiving the flushed debris and transporting the debris to the waste outlet 408 at the proximal end of the conduit. In some examples, suction is provided at the proximal end of the conduit 404 to facilitate the removal of debris. The rapid removal of debris helps to refresh the cavitation.

Figure 5:
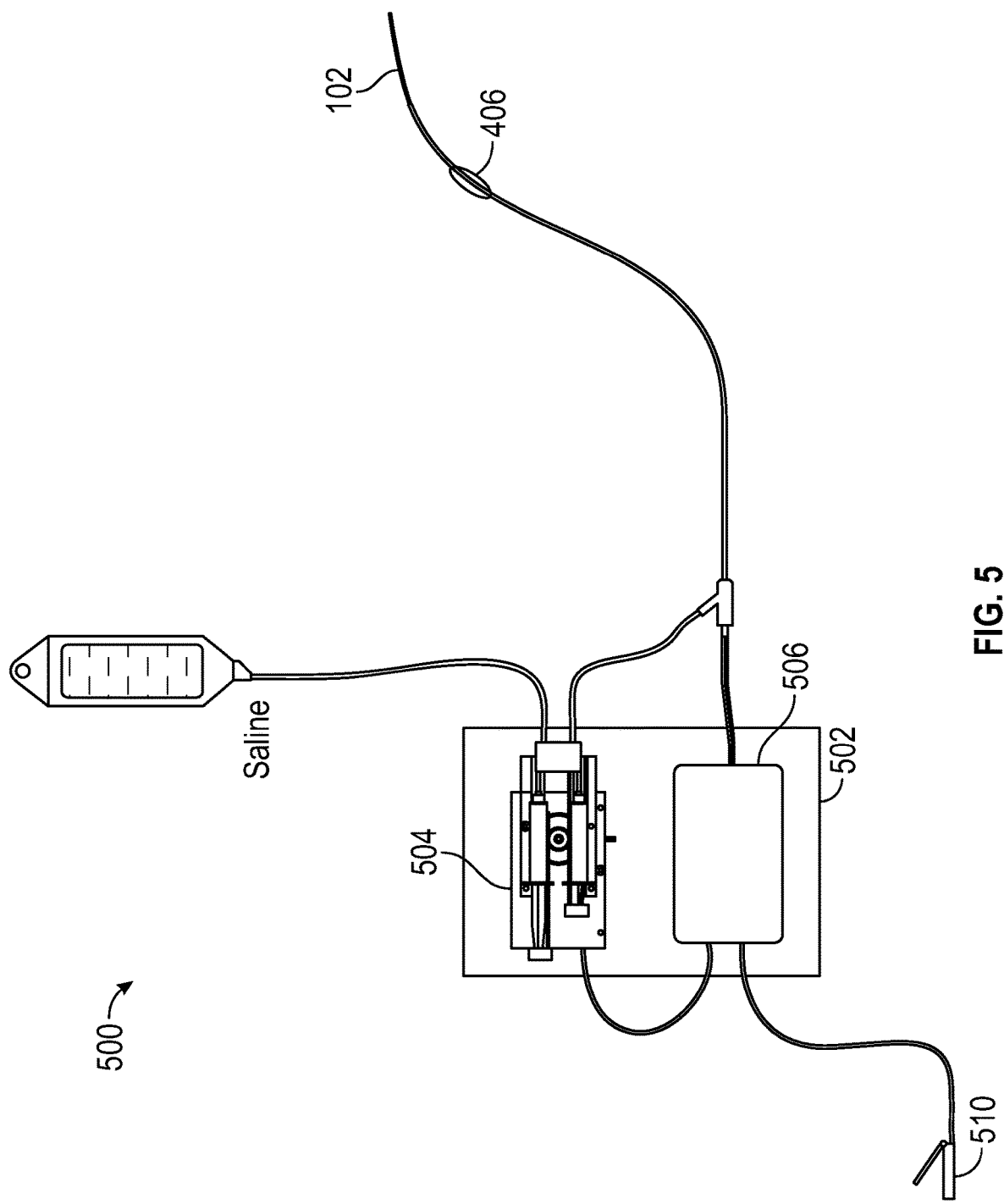
FIG. 5 is a schematic view of an exemplary system for treating an occlusion, in accordance with some embodiments.

FIG. 5 is a schematic view of an exemplary system 500 for treating an occlusion, illustrating further aspects of the invention. The system 500 further includes a control console 502 having an infusion pump 504 and a generator 506. The infusion pump provides the flow of conductive fluid (e.g., saline) toward the forward bubble generating tip via the irrigation lumen. In some examples, an auxiliary pump may be used for aspiration and removal of debris. The generator serves as a voltage supply for the electrodes at the forward bubble generating tip. The pulses have a voltage in the range of 500 to 3000 volts and more preferably 600 to 1000 volts. Ideal electrical energies applied for CTO crossing are very low (between 5 and 50 mJ per pulse) to avoid generating excess heat, and more preferably 30 mJ. Current ranges from 1-15 Amperes. The pulses are generated with a repetition rate in the range of 14 to 800 Hz. In some examples, the system further includes a visualization system and/or a steering system for properly navigating (e.g., side branches) and placing the forward bubble generating tip. Alternatively or additionally, the forward bubble generating tip could be made of a radiopaque material that is easy to see under fluoroscopic guidance. Thus, instead of steel, materials filled with Barium sulfate, tungsten or other radiopaque materials, or materials filled with radiopaque materials can be used so that the device can be tracked.

In use, a guidewire can be advanced through the central open region in the device and towards the hole drilled or being drilled in the occlusion. For example, the guidewire can be advanced through the drilled hole to guide the advancement of the treatment system, which continues drilling until the occlusion is crossed. In some examples, the guidewire can be advanced through the elongated conductive tube (e.g., from saline inlet 402), more specifically, through the center of the coiled portion of the bubble generating tip. After the occlusion is crossed, the forward bubble generating tip can be withdrawn, while the guidewire can remain to allow the access of other tools such as angioplasty or Lithoplasty™ balloons using over the wire entry. Lithoplasty is the trademark of assignee directed to its intravascular lithotripsy (shock wave) catheters. As discussed below, after the hole is drilled, an angioplasty balloon catheter can be advanced through the drilled hole to a distal end of the occlusion and aligned with the occlusion.

Figure 6:
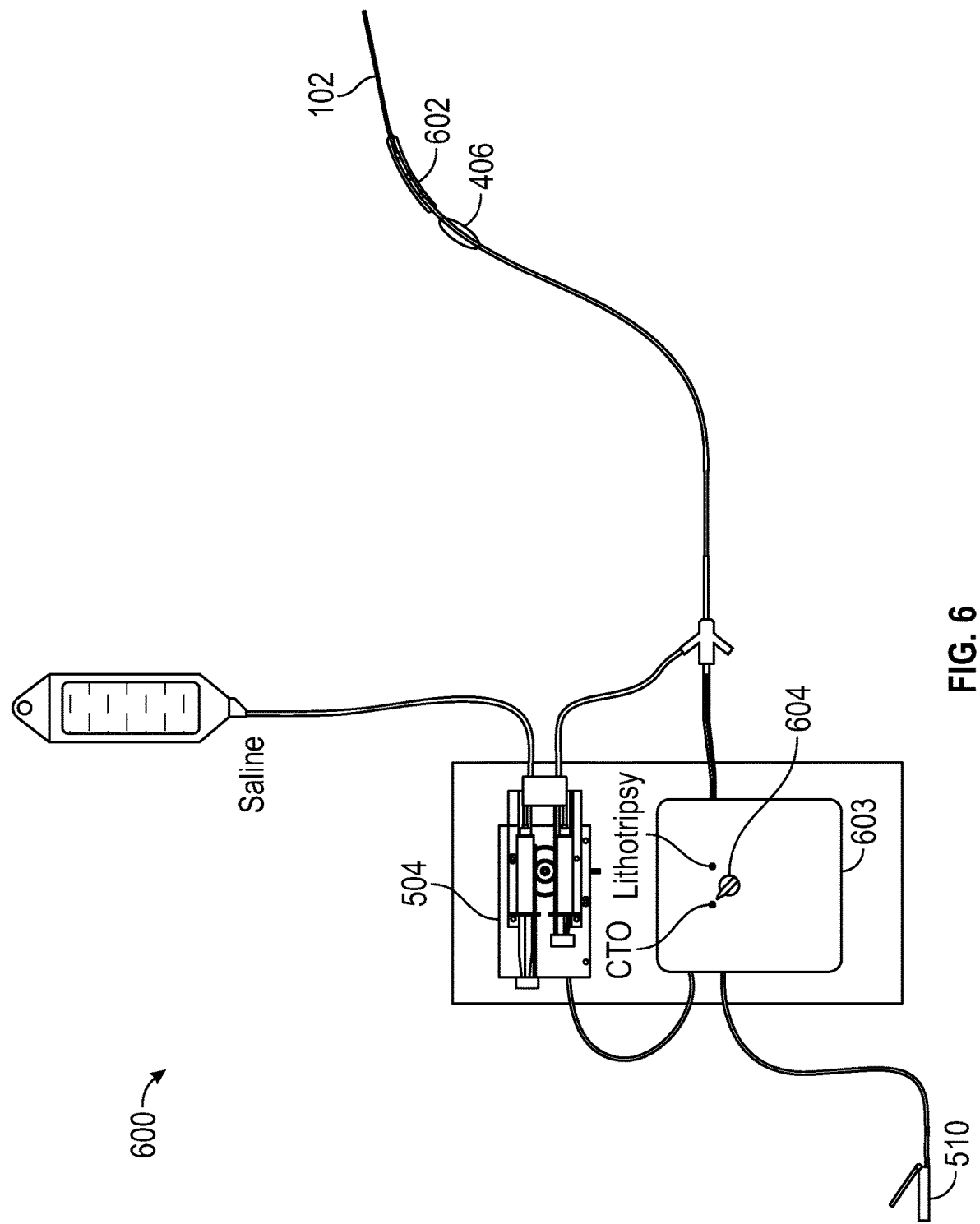
FIG. 6 is a schematic view of another exemplary system for treating an occlusion, in accordance with some embodiments.

FIG. 6 is a schematic view of another exemplary system 600 for treating an occlusion, in accordance with some embodiments. The treatment system can be used alone or in conjunction with an angioplasty balloon 602. In some examples, the forward bubble generating tip is first advanced within a lumen (e.g., blood vessel or ureter) to contact the occlusion to drill a hole through the occlusion in accordance with processes described above. Thereafter, the balloon is advanced to the lesion. The balloon 602 is then pressurized with a fluid to expand the lumen to enhance flow (e.g., blood flow). As noted above, the advancement and positioning of the balloon can be aided with a guidewire passed through the center of the device.

As an alternative, the angioplasty balloon is a lithotripsy balloon and a shock wave generator may be disposed within the balloon 602. The shock wave generator may take the form of, for example, a pair of electrodes. When the balloon 602 is aligned with the distal end of the occlusion and a high voltage pulse is applied across the electrodes, a shock wave is formed that propagates through the fluid and impinges upon the wall of the balloon and the occlusion. Repeated shock waves break up the occlusion without damaging surrounding soft tissues. In some examples, the shock waves can be generated along an axis perpendicular to the axis of the catheter (instead of being forwardly directed) so that they treat different parts of the occlusion. The angioplasty balloon 602 can then be expanded to further open up the lumen. As depicted in FIG. 6, the control console 603 includes a selector switch 604 for selecting between "CTO" and "Lithoplasty™" for switching the voltage supply between providing lower voltage pulses to the forward bubble generating tip and providing higher voltage pulses to the shock wave generator within the balloon 602. In this example, the proximal balloon can be placed on either side of the lithotripsy balloon.

Figure 7:
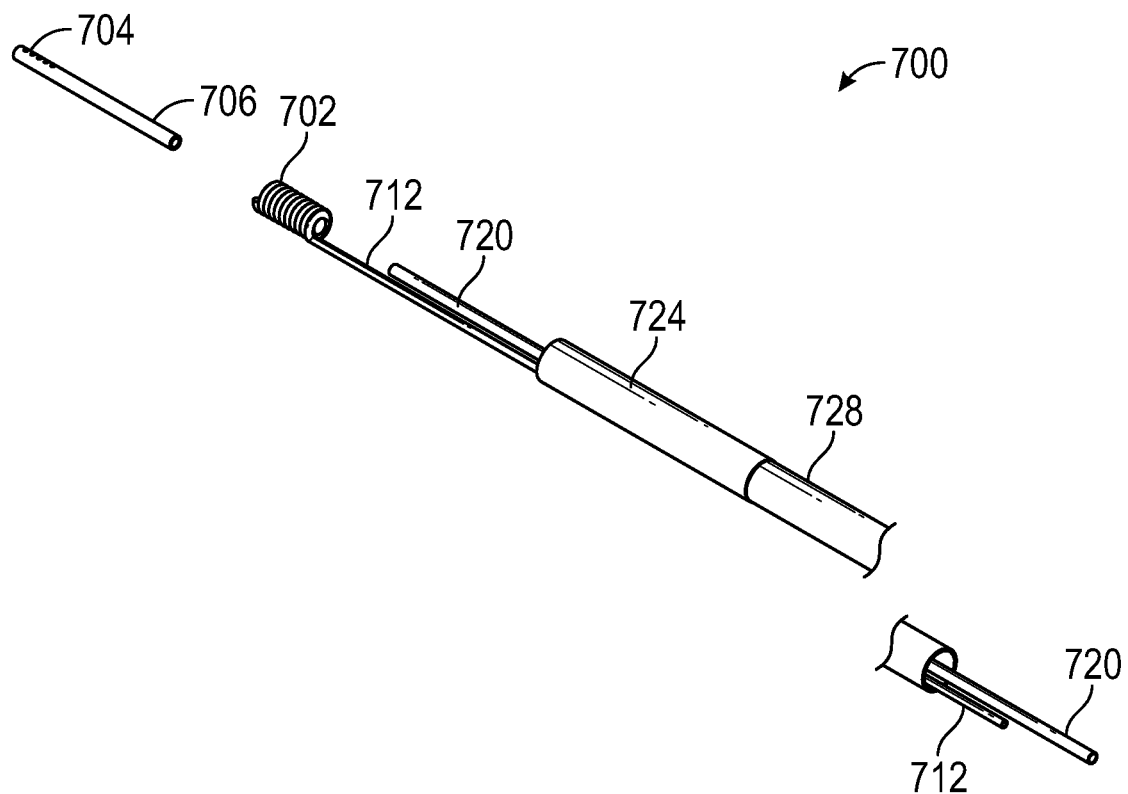
FIG. 7 is an expanded view of another exemplary system for treating an occlusion, in accordance with some embodiments.
Figure 8:
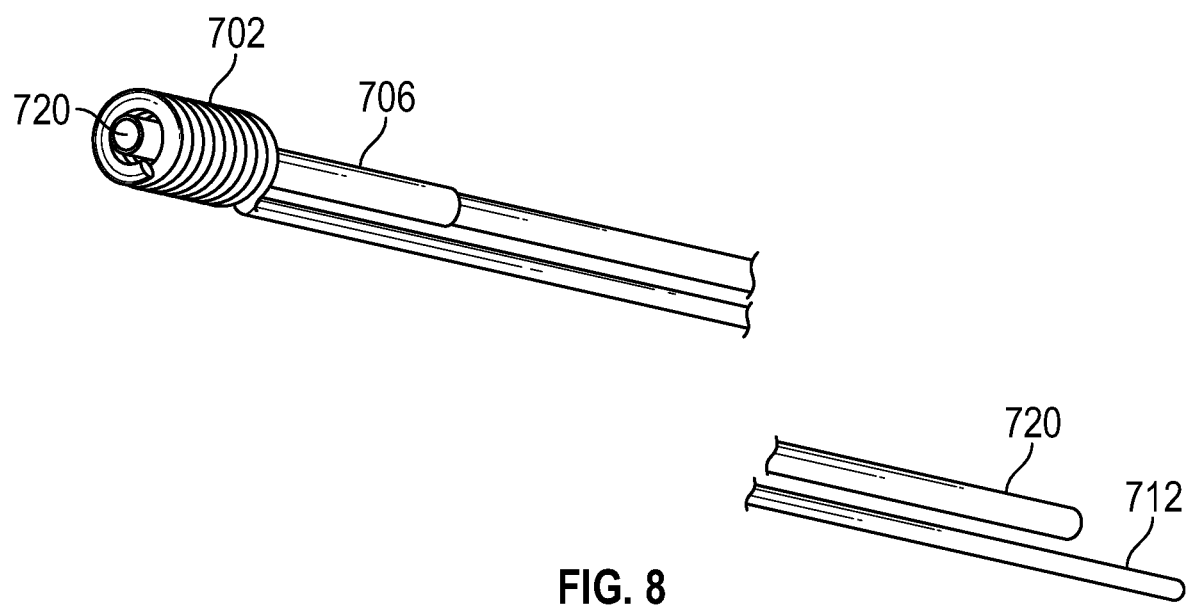
FIG. 8 is a perspective view of the system of FIG. 7.

FIGS. 7 to 9 represent an alternate embodiment of the subject treatment system. Similar to the previous embodiments, the embodiment of FIGS. 7 to 9 includes a helically coiled portion 702 at the distal end of an insulated wire 712. In addition, the distal end of the coil is not insulated and forms one electrode. Unlike the previous embodiments that included a second conductor in the form of an outer cylindrical tube, in this embodiment, the second conductor is in the form of a cylindrical central electrode 720.

The distal end of the central electrode 720 is received within the coiled portion 702 of the insulated wire. In the preferred embodiment, an insulated tube 706 surrounds the distal end of the central electrode. The insulated tube includes a plurality of holes 704 that provide additional pathways for conducting current as the coiled portion of the insulated wire erodes during use. In a preferred embodiment, an annular channel 730 is formed between the outer surface of the insulated tube 706 and the inner surface of the coiled portion 702. This channel can be used to supply conductive fluid to the distal tip of the device. Since the wire 712 is insulated, it may be possible to configure the device without the insulated tube 706.

A cylindrical outer shell 724 surrounds the distal end of the device. The shell can be formed from a metal such as stainless steel. Alternatively, the shell could be made from a non-metal such as Polyether ether ketone (PEEK) or a polyimide-based plastics such as Vespel198 . The material should be heat resistant and provide some stiffness for crossing the occlusion. The proximal end portion of the outer shell (728), is formed from a more flexible material to facilitate advancement of the device through the circulatory system.

The embodiment of FIGS. 7 to 9 would be used in a manner similar to the previously discussed embodiments. Briefly, the proximal ends of the insulated wire and central electrode are connected to a power source generating pulses with a repetition rate on the order of hundreds of pulses per second. The pulses create cavitation bubbles in the conductive fluid at the distal end of the device. The cavitation bubbles create mechanical vibrations that can chip away at the occlusion.

As in the previous embodiments, during operation, the end of the coiled portion of the insulate wire will typically erode. As the wire erodes, the point at which the cavitation bubbles are generated moves circumferentially about the periphery of the central electrode. As noted above, the holes 704 in the insulated tube 706 provide sequential pathways for the current as the coiled wire erodes.

In a preferred embodiment, the central electrode 720 is removably mounted within the device. In use, after the occlusion has been opened, the central electrode can be removed providing a channel for insertion of a guidewire or other device for further treatment.

FIG. 10 illustrates a variant of the embodiment of FIGS. 7 to 9. In this embodiment, the outer surface of the insulated tube 706 includes radially projecting spacers 740. The spacers 740 function to space the central electrode 720 from the inner surface of the coiled portion 702 of insulated wire 712.

It will be understood that the foregoing is only illustrative of the principles of the invention, and that various modifications, alterations and combinations can be made by those skilled in the art without departing from the scope and spirit of the invention. For example, the foregoing principles can applied to treat occlusions formed in any part of the body. Any of the variations of the various treatment systems disclosed herein can include features described by any other treatment systems or combination of treatment systems herein. Furthermore, any of the methods can be used with any of the treatment systems disclosed. Accordingly, it is not intended that the invention be limited, except as by the appended claims. For all of the variations described above, the steps of the methods need not be performed sequentially.

What is claimed is:

1. A system for treating an occlusion within a body lumen, comprising:
    an insulated outer sheath;
    an elongated conductive tube mounted within a distal end of the insulated outer sheath;
    a conductive wire;
    an insulating coating applied circumferentially and continuously around the conductive wire, the distal end of the circumferentially coated wire forming a helically coiled portion, with the adjacent side surfaces of the turns of the coiled portion being electrically isolated from each other by the insulating coating;
    wherein the coiled portion of the circumferentially coated wire includes an exposed distal tip at the distal end of the coiled portion;
    wherein the coiled portion is positioned within a distal portion of the elongated conductive tube;
    wherein a central region of the coiled portion defines an open passage capable of receiving a conductive fluid; and
    wherein, when voltage pulses are applied across the insulated wire and the elongated conductive tube, a current is configured to flow from the exposed distal tip of the insulated wire to the elongated conductive tube to generate a plurality of cavitation bubbles.

2. The system claim 1, further comprising an insulated layer disposed between the coiled portion of the insulated wire and the elongated conductive tube.

3. The system of claim 2, wherein the insulated layer includes a plurality of holes arranged along a longitudinal axis of the insulated layer.

4. The system of claim 3, wherein a plurality of plasma arcs are generated across a hole of the plurality of holes arranged on the insulated layer.

5. The system of claim 2, wherein a plurality of plasma arcs are generated across a distal edge of the insulated layer.

6. The system of claim 2, further comprising a plurality of spikes at a distal end of the elongated conductive tube, wherein the plurality of spikes are configured to cause a plurality of plasma arcs to be generated across a distal edge of the insulated layer.

7. The system of claim 1, wherein the elongated conductive tube is connected to a ground wire.

8. The system of claim 7, further comprising a voltage supply connected to a proximal end of the ground wire and a proximal end of the insulated wire.

9. The system of claim 1, wherein the insulated outer sheath includes an inlet for receiving conductive fluid.

10. The system of claim 9, further comprising:
    a proximal balloon mounted over a length of the insulated outer sheath; and
    a waste conduit for receiving debris carried by the conductive fluid.

11. The system of claim 1, further comprising a plurality of tines at a distal end of the elongated conductive tube, wherein the plurality of tines are configured to prevent the distal end of the elongated conductive tube from perforating the lumen.

12. The system of claim 1, wherein a distal end of the elongated conductive tube is configured to extend beyond the distal tip of the coiled portion of the insulated wire such that the plurality of cavitation bubbles are generated in a forward direction toward the occlusion.

13. The system of claim 1, wherein the plurality of cavitation bubbles are configured to generate mechanical vibrations at a vibration rate ranging from 14 Hz to 800 Hz.

14. A method for treating an occlusion within a body lumen, comprising:
advancing a treatment device within the lumen to contact the occlusion, wherein the treatment device comprises:
an insulated outer sheath;
an elongated conductive tube mounted within a distal end of the outer sheath;
an insulated wire having a helically coiled portion at a distal end of the insulated wire, wherein the coiled portion includes an exposed distal tip and wherein the coiled portion is positioned within a distal portion of the elongated conductive tube; and wherein a central region of the coiled portion defines an open passage; and
injecting conductive fluid into a proximal end of the outer sheath, said conductive fluid passing through the open passage in the coiled portion and exiting the distal end of the outer sheath; and
applying voltage pulses across the insulated wire and the elongated conductive tube to cause a current to flow from the exposed distal tip of the insulated wire to the elongated conductive tube to generate a plurality of cavitation bubbles in the conductive fluid.

15. The method of claim 14, wherein the treatment device further comprises a proximal balloon connected to a waste inlet, the method further comprising:
while generating the plurality of cavitation bubbles, receiving debris carried by the injected conductive fluid at the waste inlet.

16. The method of claim 14, wherein the plurality of cavitation bubbles are configured to drill a hole through the occlusion.

17. The method of claim 16, further comprising:
advancing an angioplasty balloon catheter through the drilled hole to align with the occlusion; and
expanding the angioplasty balloon.

18. The method of claim 17, further comprising: prior to expanding the angioplasty balloon, generating one or more shockwaves from inside the balloon along an axis perpendicular to an axis of the catheter.

19. The method of claim 16, further comprising:
advancing a guidewire through the drilled hole via the open passage of the coiled portion of the insulated wire; and
advancing one or more tools over the guidewire.

20. The method of claim 14, wherein the lumen is a blood vessel.

21. The method of claim 14, wherein the lumen is a ureter.

22. A system for treating an occlusion within a body lumen, comprising:
an insulated outer sheath;
a fluid source for injecting conductive fluid into a proximal end of the outer sheath, with the conductive fluid exiting a distal end of the outer sheath;
an elongated conductive tube mounted within the distal end of the insulated outer sheath;
a conductive wire
an insulating coating applied circumferentially and continuously around the conductive wire, the distal end of the circumferentially coated wire forming a helically coiled portion, with the adjacent side surfaces of the turns of the coiled portion being electrically isolated from each other by the insulating coating;
wherein the coiled portion of the circumferentially coated wire includes an exposed distal tip at the distal end of the coiled portion;
wherein the coiled portion is positioned within a distal portion of the elongated conductive tube;
wherein a central region of the coiled portion defines an open passage through which the conductive fluid passes; and
wherein, when voltage pulses are applied across the insulated wire and the elongated conductive tube, a current is configured to flow from the exposed distal tip of the insulated wire to the elongated conductive tube to generate a plurality of cavitation bubbles in the conductive fluid.

23. The system claim 22, further comprising an insulated layer disposed between the coiled portion of the insulated wire and the elongated conductive tube.

24. The system of claim 23, wherein the insulated layer includes a plurality of holes arranged along a longitudinal axis of the insulated layer.

25. The system of claim 24, wherein a plurality of plasma arcs are generated across a hole of the plurality of holes arranged on the insulated layer.

26. The system of claim 22, wherein the elongated conductive tube is connected to a ground wire.

27. The system of claim 26, further comprising a voltage supply connected to a proximal end of the ground wire and a proximal end of the insulated wire.

28. The system of claim 27 wherein said voltage supply generates pulses having a frequency between 14 and 800 hertz.

29. The system of claim 22, further comprising a plurality of tines at a distal end of the elongated conductive tube, wherein the plurality of tines are configured to prevent the distal end of the elongated conductive tube from perforating the lumen.

30. The system of claim 22, wherein a distal end of the elongated conductive tube is configured to extend beyond the distal tip of the coiled portion of the insulated wire such that the plurality of cavitation bubbles are generated in a forward direction toward the occlusion.

* * * * *